US008304253B2

(12) United States Patent
Yi et al.

(10) Patent No.: US 8,304,253 B2
(45) Date of Patent: Nov. 6, 2012

(54) DROPLET EXTRACTION FROM A LIQUID COLUMN FOR ON-CHIP MICROFLUIDICS

(75) Inventors: Uichong Brandon Yi, Los Angeles, CA (US); Peter Patrick De Guzman, Orange, CA (US); Wayne Liu, Los Angeles, CA (US); Chang-Jin Kim, Beverly Hills, CA (US)

(73) Assignee: Advanced Liquid Logic Inc, Research Triangle Park, NC (US)

( * ) Notice: Subject to any disclaimer, the term of this patent is extended or adjusted under 35 U.S.C. 154(b) by 356 days.

(21) Appl. No.: 12/090,922

(22) PCT Filed: Oct. 19, 2006

(86) PCT No.: PCT/US2006/060078
§ 371 (c)(1),
(2), (4) Date: Sep. 11, 2008

(87) PCT Pub. No.: WO2007/048111
PCT Pub. Date: Apr. 26, 2007

(65) Prior Publication Data
US 2009/0014394 A1 Jan. 15, 2009

Related U.S. Application Data

(60) Provisional application No. 60/728,985, filed on Oct. 22, 2005.

(51) Int. Cl.
*B01D 57/00* (2006.01)
*B01L 99/00* (2010.01)
(52) U.S. Cl. ........ 436/177; 436/174; 436/180; 422/500; 422/502; 422/504
(58) Field of Classification Search .................. 204/604, 204/600, 601, 602, 603; 436/52, 53, 43, 436/174, 175, 177, 178, 180; 422/81, 82, 422/422/68.1, 70, 69, 500, 502, 503, 504, 422/505, 506, 507
See application file for complete search history.

(56) References Cited

U.S. PATENT DOCUMENTS 5,846,396 A 12/1998 Zanzucchi et al.
(Continued)

OTHER PUBLICATIONS

Cho, Sung Kwon, et al. "Creating, transporting, cutting, and merging liquid droplets by electrowetting-based actuation for digital microfluidic circuits." Journal of Microelectromechanical Systems (2003) 12 p. 70-80.*

(Continued)

*Primary Examiner* — Yelena G Gakh
*Assistant Examiner* — Christopher A Hixson
(74) *Attorney, Agent, or Firm* — Ward & Smith P.A.; William A. Barrett

(57) ABSTRACT

A refill droplet facilitates the extraction of a droplet laterally from a channel in a microfluidic apparatus. Such extraction allows a discrete band of separated particles or solute molecules to be excised from a fluid stream and processed and analyzed separately. An extraction point is located along the length of the channel and includes an EWOD surface or similar microfluidic technology to extract a droplet. An opening in the channel opposite the extraction means is equipped with microfluidic technology to transport a refill droplet to the opening. The refill droplet is moved into the channel or column to occupy the area previously occupied by the extracted droplet. This prevents distortion or mixing of the bands of particles or molecules within the channel and prevents the draining of any portion of the fluidic system.

8 Claims, 4 Drawing Sheets

U.S. PATENT DOCUMENTS

| | | | |
|---|---|---|---|
| 2003/0007898 A1* | 1/2003 | Bohm et al. | 422/100 |
| 2004/0014102 A1 | 1/2004 | Chen et al. | |
| 2004/0058450 A1* | 3/2004 | Pamula et al. | 436/150 |
| 2004/0155926 A1* | 8/2004 | Silverbrook | 347/54 |

OTHER PUBLICATIONS

Fu, L.-M., et al. "Electrokinetic injection techniques in microfluidic chips." Analytical Chemistry (2002) 74 p. 5084-5091.*

Cho, Sung Kwon et al. "Particle separation and concentration control for digital microfluidic systems." IEEE Conf. MEMS, Kyoto, Japan (2003) p. 686-689.*

Cho, et al. "Creating, transporting, cutting, and merging liquid droplets by electrowetting-based actuation for digital microfluidic circuits." Journal of Microelectromechanical Systems (2003) 12 70-80.*

R.B. Fair, V. Srinivasan, H. Ren, P. Paik, V.K. Pamula, M.G. Pollack, "Electrowetting-based On-Chip Sample Processing for Integrated Microfluidics," IEEE Inter. Electron Devices Meeting (IEDM), pp. 32.5.1-32.5.4, 2003.

Pollack et al., "Electrowetting-based actuation of liquid droplets for microfluidic applications," Appl. Phys. Letters, vol. 77, No. 1 (Sep. 11, 2000), pp. 1725-1726.

Masao Washizu, "Electrostatic Actuation of Liquid Droplets for Micro-Reactor Applications", IEEE Industry Applications Society Annual Meeting, pp. 1867-1873, Oct. 5-9, 1997.

Jie Ding, "System level architectural optimization of semi-reconfigurable microfluidic system," M.S. Thesis, Duke University Dept of Electrical Engineering, 2000.

Moon, Hyejin, Ph.D., "Electrowetting-on-dielectric microfluidics: Modeling, physics, and MALDI application," University of California, Los Angeles, 2005.

Mugele et al., "Electrowetting: from basics to applications," Journal of Physics: Condensed Matter, 17, pp. R705-R774 (Jul. 2005).

T. Taniguchi et al., "Chemical reactions in microdroplets by electrostatic manipulation of droplets in liquid media," Lab on a Chip, vol. 2, No. 2, pp. 19-23 (2002).

Hyejin Moon, "Electrowetting-On-Dielectric Microfluidics: Modeling, Physics, and MALDI Application," Ph.D. Dissertation, University of California Dept. of Mechanical Engineering, published Aug. 2006.

\* cited by examiner

A

B

C

US 8,304,253 B2

DROPLET EXTRACTION FROM A LIQUID COLUMN FOR ON-CHIP MICROFLUIDICS

CROSS-REFERENCE TO PRIOR APPLICATIONS

The present application is the non-provisional version of U.S. Provisional Patent Application 60/728,985, filed on 22 Oct. 2005, and claims the benefit and priority of that application.

GRANT INFORMATION

This invention was made with government support under NBCHC-05-0123 and NBCHC-06-0082 awarded by Department of Homeland Security Advanced Research Projects Agency (HSARPA). The government has certain rights in the invention.

BACKGROUND OF THE INVENTION

1. Area of the Art

The present invention concerns the art of microfluidics—namely the transport and processing of fluid samples on a micro-scale.

2. Description of the Background Art

This invention addresses the problem of extracting sample droplets from liquid columns by means of surface phenomena, particularly by means of electrowetting, to enable multi-staged separation and analysis functions external to the original microfluidic circuit. Digital Microfluidics (see, "Creating, Transporting, Cutting, and Merging Liquid Droplets by Electrowetting-Based Actuation for Digital Microfluidic Circuits" Sung Kwon Cho, Hyejin Moon, and Chang-Jin Kim, *Journal of Microelectromechanical Systems*, V. 12, NO. 1, February 2003, pp. 70-80; and M. G. Pollack, R. B. Fair, and A. D. Shenderov, "Electrowetting-based actuation of liquid droplets for microfluidic applications," *Appl. Phys. Lett., vol.* 77, no. 11, pp. 1725-1726, 2000) is used as an example technology for demonstrating on chip droplet extraction. One of ordinary skill in the art will recognize that the present invention is applicable to a number of fluidic technologies where a fluid is transported in a channel, or column, and it is desired to remove a sample of the fluid without disturbing the overall transport. "Column" includes the usual devices of fluidic conveyance such as a channel, pipe, or capillary (e.g., a tube where physical walls constrain the fluid) as well as any configuration whereby a fluid is made to flow in a directed stream (e.g., a surface where surface properties constrain a flowing film of fluid to a portion of that surface). The liquid column can be formed by any arrangement that bounds or constrains the liquid flow in a particular direction or pathway, such as filling a liquid in a channel (e.g., physical walls constraining the fluid) or by applying non-uniform surface properties and effects to create a directional affinity for the liquid column (e.g. no physical walls)

In many cases the fluid column is designed not just to transport fluid but to separate and concentrate solute molecules or particles within the fluid. Many fluidic analysis systems and sensor chips (e.g., those useful in chem-bio, that is, chemistry and biology applications) utilize continuous liquid columns to transport as well as to separate and analyze fluidic samples. For example, microfluidic sensor chips often rely on walled liquid columns (microchannels) to transport and facilitate separation of a sample fluid into concentrated bands or zones of solute molecules or suspended particles by means of capillary electrophoresis (CE), Dielectrophoretic separation (DEP) and other separation techniques. Evaluation of the concentrated bands resulting is typically conducted within (or at the end of) the liquid column by using a variety of optical, electrical or chemical analytical systems. To reduce the probability of error, it is desirable to evaluate the separated band with secondary separation and analytic devices. However, these secondary instruments are often not co-located with or in close proximity to the primary analytical device; rather they may be located downstream or external to the channel-structure and thus require the transport or transfer of the concentrated band from the primary analytical device to such secondary locations. The subsequent transport of the band to these secondary evaluation stations is difficult to achieve without disturbing the column of fluid in the primary channel thereby incurring unwanted diffusion or pressure-driven dispersion of the concentrated molecules or particles. Thus, in order to integrate or operate with multi-staged separation and analysis stations, it is essential to precisely excise discrete portions of the primary fluid column and preserve the concentrated bands during transport between analysis stations.

SUMMARY OF THE INVENTION

An inventive microfluidic device and method use a refill droplet to facilitate the extraction of a droplet from a channel or separation column in a microfluidic apparatus. There are many instances where it is advantageous to extract a portion of a fluid stream from a microfluidic channel or column. Such extraction allows a discrete band of separated particles or solute molecules to be excised from a fluid stream and processed and analyzed separately. The channel or separation column may be bounded by physical walls or it may exist on the surface of a fluidic device with its boundaries defined by differences in surface properties of the surface. An extraction point is located along the length of the column or channel. If the column or channel is enclosed by physical walls, the extraction point includes openings through the wall.

At the extraction point means are provided on one side of the column or channel to extract a segment of fluid from the channel or column. This is accomplished by providing an EWOD surface or other microfluidic technology for driving droplets adjacent the extraction point. Generally, the extraction point also includes an opening in the channel or column wall opposite the extraction means. This opening is equipped with an EWOD surface or other means to transport a refill droplet to the opening opposite the extraction means. When the extraction means attempts to pull a volume of fluid from the column or channel, the cohesive nature of water molecules resists this force and exerts an opposite "pull back" force. If the droplet is nevertheless extracted, the other bands of separated particles or molecules within the column or channel become mixed or distorted. Further, part or all of the contents of the channel or column may follow the extracted droplet effectively draining a portion of the microfluidic system. The refill droplet obviates this problem by neutralizing the "pull back" force and stabilizing the fluid stream within the column or channel. As the extraction means pulls the droplet out one side of the column or channel, the refill droplet is moved into the channel or column to occupy the area previously occupied by the extracted droplet. This prevents distortion or mixing of the bands of particles or molecules within the column or channel and prevents the draining of any portion of the fluidic system.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a method of extracting a single droplet from a separation column or channel in a microfluidic device.

The present invention solves this problem by integrating liquid column-based transport and separation functions with Digital Microfluidic droplet handling to extract a mobile droplet that has been enriched with column-concentrated solute molecules. Extraction of a solute-rich droplet enables additional follow-on operations to be applied to the enriched sample volume, such as further in-droplet sample purifications (see e.g., "Particle Separation and Concentration Control for Digital Microfluidic Systems," Sung Kwon Cho and Chang-Jin "C J" Kim, *IEEE Conf. MEMS*, Kyoto, Japan, January 2003, pp. 686-689) and/or droplet transfer to a secondary analysis or imaging site without dilution of the concentrated solute molecules.

Figure 1:
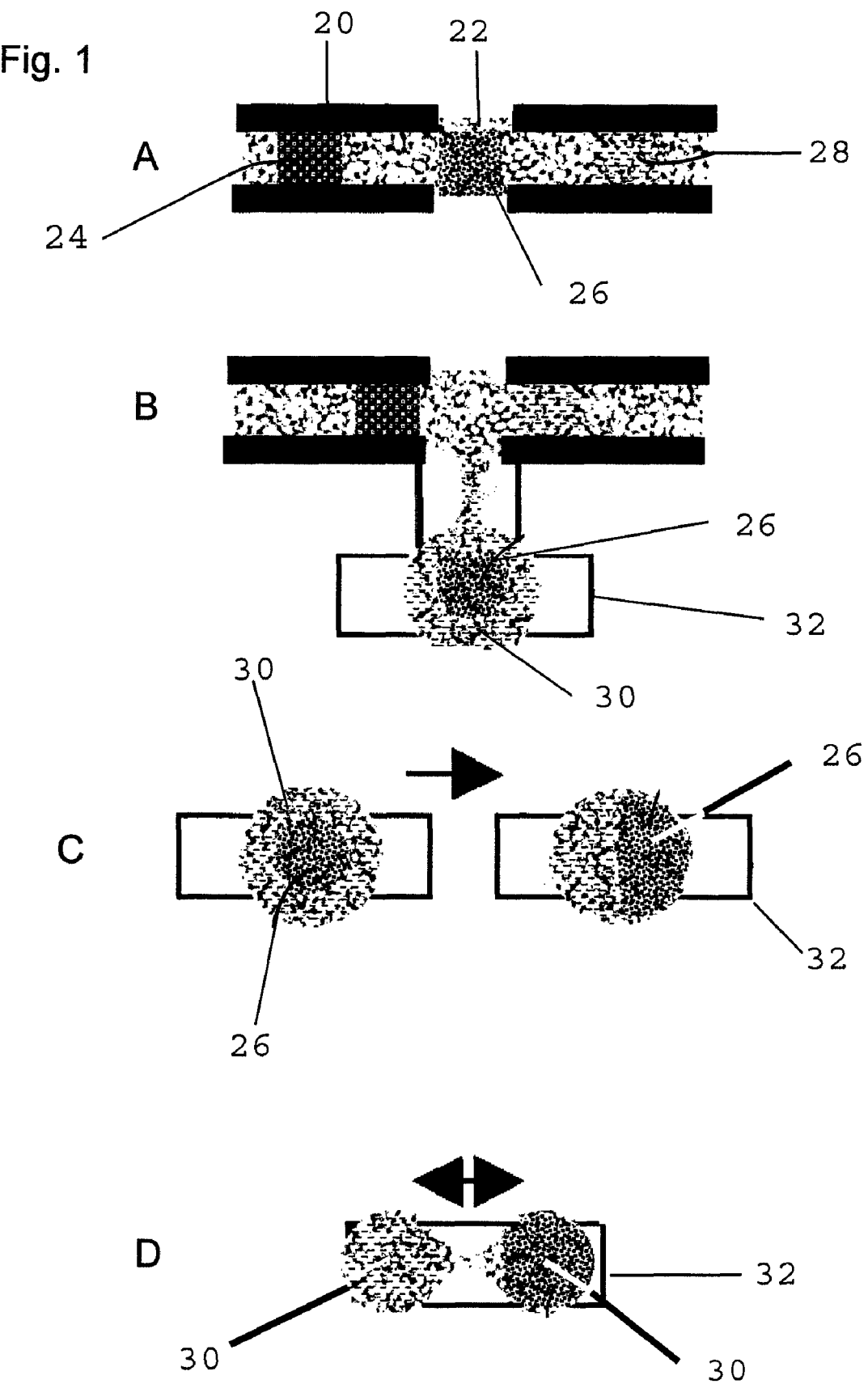
FIG. 1 shows a diagrammatic representation of channel-to-droplet extraction achieved by integrating liquid-column based separation and Digital Microfluidics to enable transport of concentrated sample droplets to secondary evaluation sites.

FIG. 1 shows the inventive process diagrammatically. FIG. 1A is a diagram of a separation column or channel shown as a tube or capillary 20 with a physical opening 22 in its side wall serving as an extraction point. In addition, fluid columns can also be bounded without physical walls, using instead surface property differences and effects to constrain and direct the column of fluid. In such a situation the "opening" would not be an opening in a physical wall and extraction could take place at any point along the column. The walled liquid column 20 in the figure is shown as containing three different populations of solute molecules or particles 24, 26 and 28. The middle population 26 is located adjacent the opening 22. In FIG. 1B this population 24 is withdrawn or extracted as a separate droplet 30. Once a droplet is extracted it can be transported along a fluidic pathway 32 to secondary evaluation sites. As shown diagrammatically in FIG. 1C, the separated droplet can also be subjected to a number of further manipulations. In the left panel of FIG. 1C the droplet 28 contains a central area of molecules 26. Surrounding these molecules are molecules originally found in population 28. The droplet is subjected to additional forces so to cause additional within droplet separations of particles or solutes—for example according to particle charges with negative charges becoming located at one end of the droplet and positive charges at the other as shown in the right panel of FIG. 1C (the arrow represents the application of an electrical field). Once there has been an end to end separation of particles or solutes, it is then possible to split the droplet 30 (FIG. 1D) into separate droplets 30' and 30" by means of applied forces (two ended arrow) so that the separated particles or solutes can be separately analyzed.

According to the present invention droplet extraction from a liquid column for on-chip microfluidics can be achieved without mechanical structures (e.g., valves or pumps) or pneumatic effects (e.g., driving the liquid by gas pressure) by using surface-borne effects such as surface acoustic waves (SAW) and control of surface wettability via electrical, optical or chemical means. A specific example of the use of surface-borne effects is droplet extraction by means of electrowetting based Digital Microfluidics.

Surface effect-based extraction of droplets can advantageously be applied to any microfluidic function that serves to transport, focus, concentrate, or separate target molecules within a column of fluid (e.g., a continuous linear fluid volume) contained within a column. Examples of such microfluidic techniques include Capillary Electrophoresis (CE), Dielectrophoretic (DEP), Liquid Chromatography, High Performance Liquid Chromatography, and capture and release mechanisms such as immuno-magnetic-separation (IMS) using beads as well as electrophoretic capture of proteins and nucleic acids. In some of these techniques, the fluid column flows resulting in separation of solutes which move more slowly (or even become immobile) relative to the flow whereas with other techniques the fluid column is relatively stationary with the solutes moving relative to the fluid to effect separation.

Figure 2:
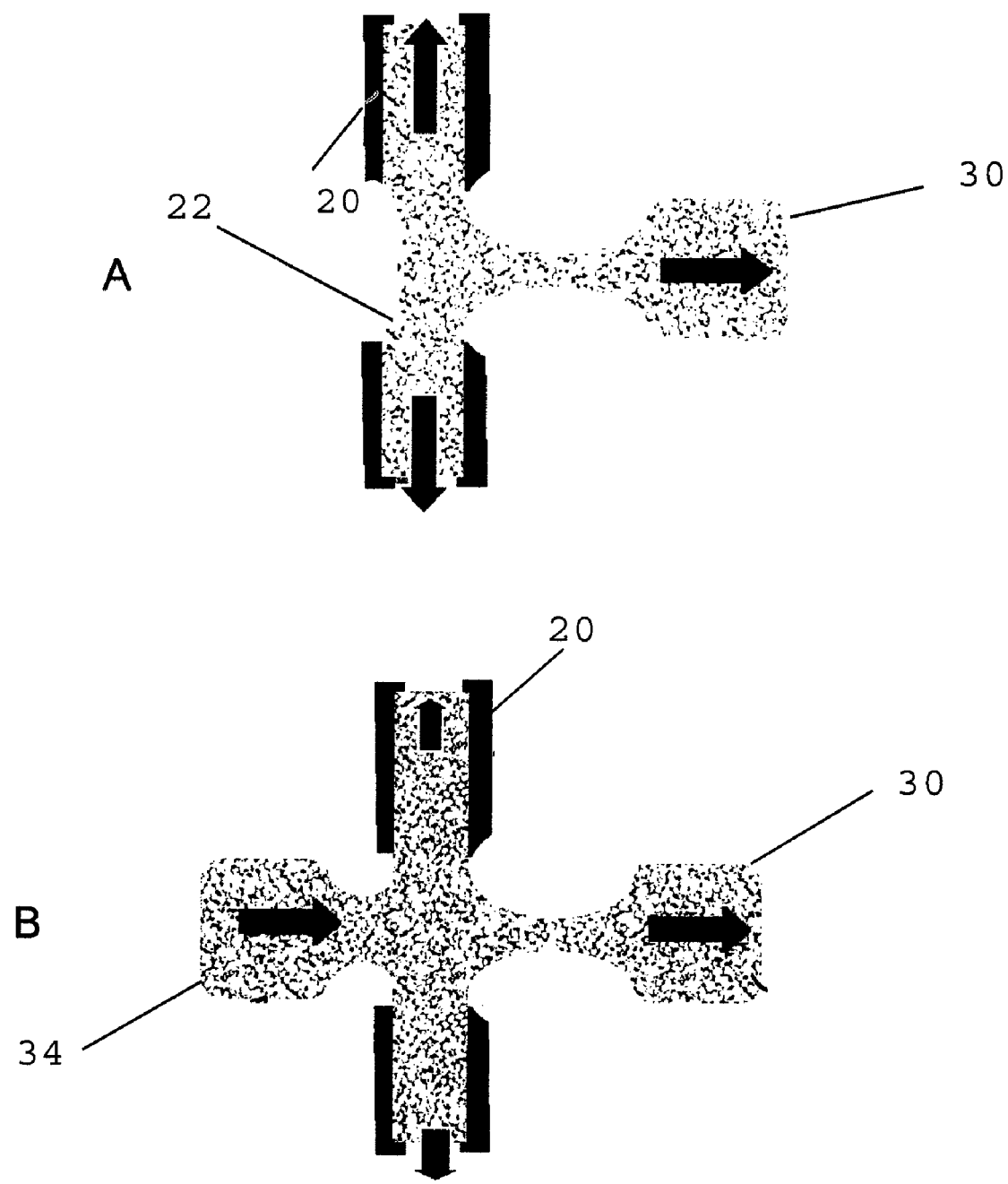
FIG. 2 is a diagrammatic representation of A) channel pull-back which resists droplet extraction and B) use of a refill droplet which mitigates channel pull-back force and replaces fluid lost via extraction to prevent drainage of channel and subsequent mixing and dilution of concentrated solute bands.

Droplet extraction can be performed anywhere along an non-walled liquid column or as shown in FIG. 2A at any wall opening in between the ends of a wall bounded liquid channel. As shown in FIG. 2A, a liquid column that is bounded by physical walls 20 will typically provide greater resistance to extraction of a droplet 30 in the form of a pull-back force (indicated by the arrows in the column 20) exerted by the intermolecular attraction or cohesion within the fluidic volume at the extraction site. If this force is not mitigated, the fluid column within the channel will be disrupted and sample molecules or particles may become mixed or otherwise disturbed and/or droplet extraction may actually be prevented. Several methods can be employed to reduce this channel pull-back force, including the merging or addition of a refill droplet 34 to the extraction site 22 as shown in FIG. 2B. The refill droplet 34 mitigates the pull-back force exerted by the column by replenishing the fluid volume lost through droplet extraction. This replenishing prevents drainage of adjacent fluids within the channel, thereby preventing the mixing and dilution of any solute bands at or near the extraction point.

Other methods may be used to mitigate channel pull back force and to replace fluid volume lost through the droplet extraction. These methods can also be used on non-walled liquid columns as the pull-back force to be mitigated in such structures will be less than with channel-bounded liquid columns.

Once a droplet is extracted, the sample within the droplet can be subjected to further separation and bifurcation manipulations and can also be split into two smaller daughter droplets (FIG. 1D) to physically isolate and drive a specific sample type to an analysis or immuno-capture site. That is, once the droplet containing sample is extracted, the droplet can be subjected to forces (e.g., electrical) to further spatially separate the sample molecules or particles within the droplet. Then the droplet can be further subdivided, for example by being pulled apart into two droplets, to render this spatial separation permanent. Alternatively, a uniform droplet can be split and divided repeatedly to create multiple identical droplets to allow parallel analysis.

Figure 3:
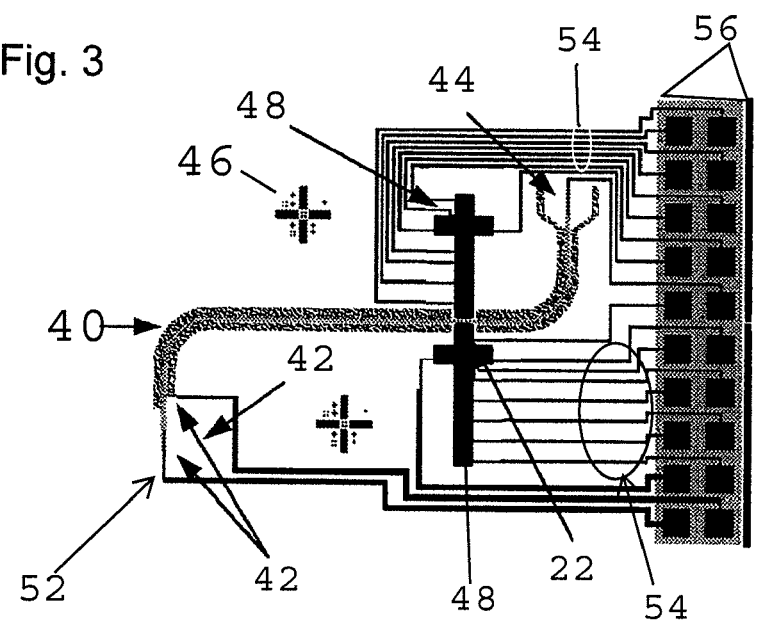
FIG. 3 is Droplet extraction test chips (3 figs
Figure 3:
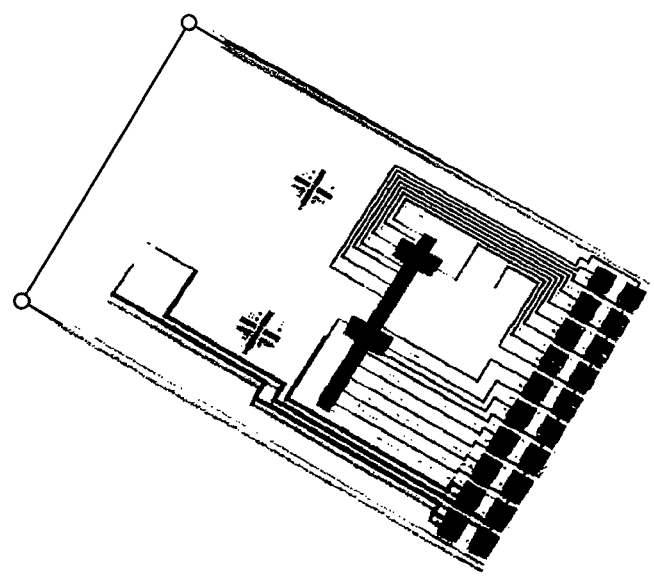
Figure 3:
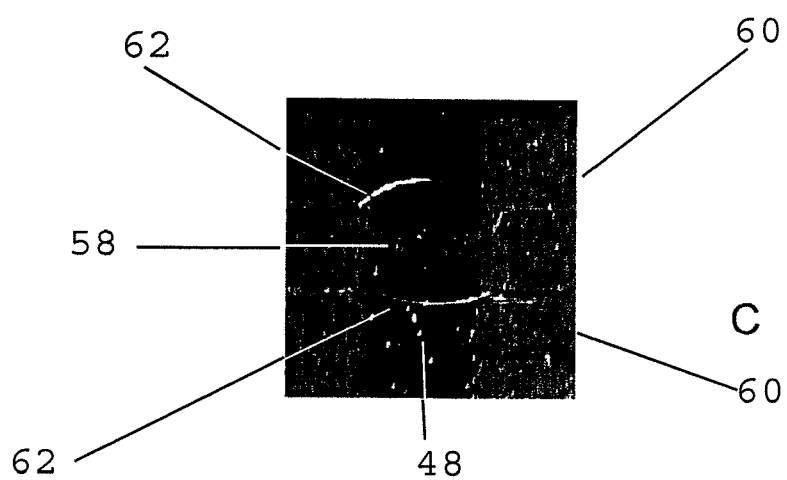

Droplet extraction from a liquid column was demonstrated using the test chip design shown in FIG. 3A. In the design the channel or column 40 is a CE column powered by CE electrodes 42 (powered by traces 52) which draw a sample from a sample reservoir 44 through the column 40. The length of the column from the reservoir 44 to the electrodes 42 is between two and three centimeters. The actual channel through which liquid flows is approximately 100 μm wide and 80 μm in height. Spacers 46 support a layer of glass (or similar transparent material) above the device to create the upper bounds of the channel. Two T-shaped EWOD electrodes 48 are provided to extract a droplet from an extraction point 22 (a 1.5 mm long opening in the walls of the column) located where the column 40 passes between the two EWOD electrodes 48. The EWOD electrodes are powered by a plurality of traces 54. All the traces lead to square connection pads 56 (20 pads total) which interconnect with a connector (not shown) to power and control the device.

FIG. 3B is a photograph of the actual fabricated chip at approximately life size. FIG. 3B shows a photomicrograph of the extraction point 22. The side walls 60 of the column end at either side of the EWOD electrodes 48 leaving the 100 μm wide fluid channel 58 to cross the electrodes 48 without side walls. In this photomicrograph, the EWOD electrodes 48 are drawing liquid out of the channel 58 forming menisci 62 on either side.

Figure 4:
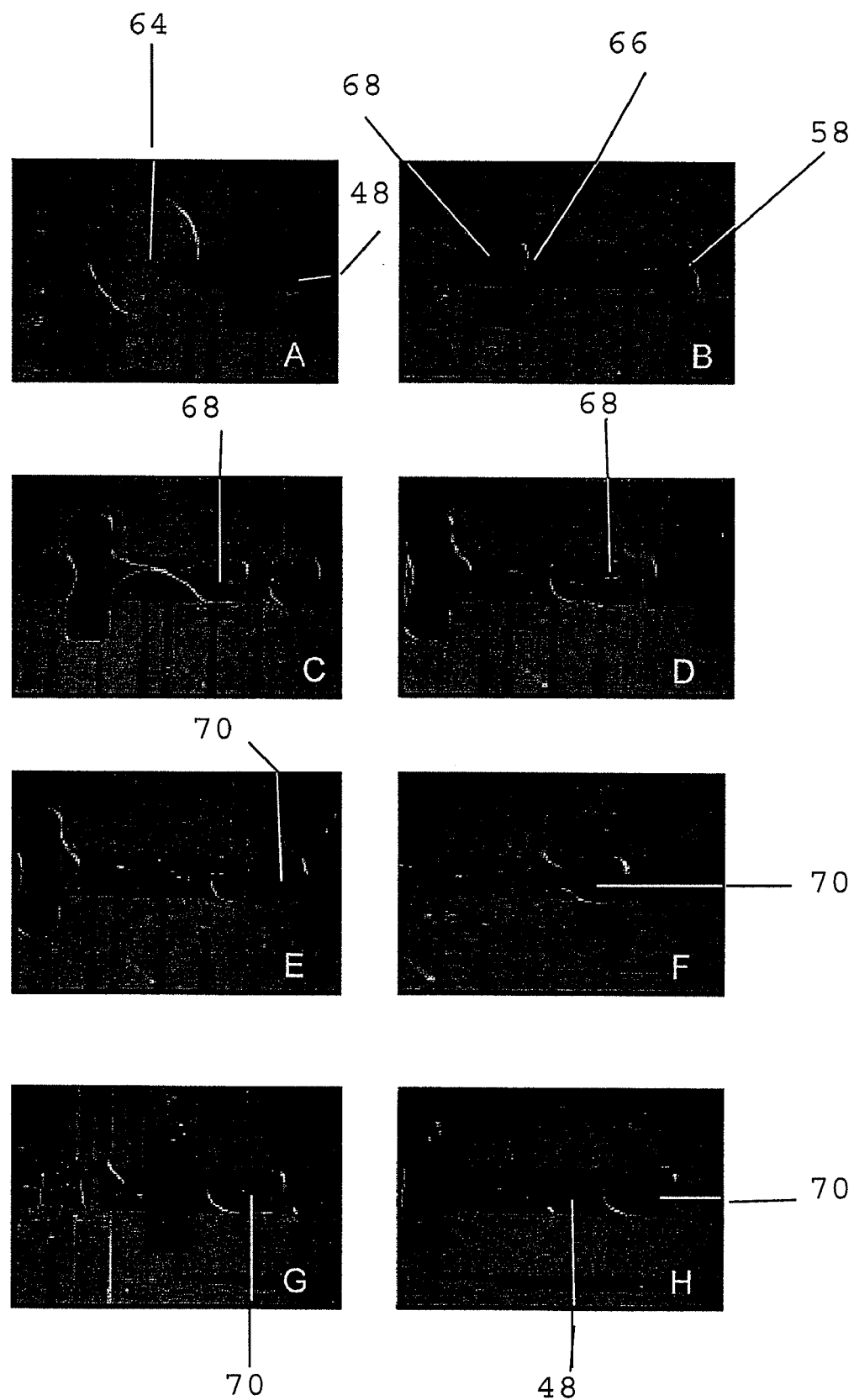
FIG. 4 shows a series of photomicrographs demonstrating the stages of droplet extraction using a test EWOD chip.

FIG. 4A shows a large reservoir water droplet 64 which will supply the refill droplet. The EWOD electrode array 48 runs from left to right. FIG. 4B shows a meniscus 66 (to the right) outlining a refill droplet 68 being pulled from the reservoir droplet 64. Note the channel 58 crossing the EWOD electrodes 48 at the far right. FIG. 4C shows the necking as the refill droplet 68 is pinched off from the reservoir droplet as the droplet 68 is driven towards the right and the channel 58. FIG. 4D shows the fully formed refill droplet 68 moving towards the separation channel 58. FIG. 4E shows a droplet 70 being extracted from the right side of the channel opening (while the refill droplet 68 moves in from the left side). FIG. 4F shows the necking of the extracted droplet 70 pulled from the separation channel 20. FIG. 4G shows the extracted drop 70 fully separated while FIG. 4H shows the extracted droplet 70 driven farther to the right end of the EWOD electrode 48.

Surprisingly, a break or physical wall opening does not interfere with liquid channel functions such as separation. For example, CE separation was successfully conducted in the test chip channel of the type shown in FIG. 3 (100 μm wide) with a mid-channel opening 1.5 mm in length. In that experiment a mixture of red colored Carboxyl Modified Latex (CML) beads (10 μm diameter) and white colored Amino Sulfate coated beads (10 μm diameter) were pipetted into the channel input reservoir. Then an approximately 80V potential was applied to the CE electrodes located at opposite ends of the channel. There was clear separation of red and white beads into distinct bands within the channel due to surface charge differences of the beads. The band of red beads arrived first at the extraction point where it was extracted following the steps shown in FIG. 4. At the extraction point the band of white beads reached the earlier arriving red beds. As anticipated remixing of the two bead populations was prevented by the droplet extraction-refill droplet process demonstrating that 1) the order of separation can be preserved and that 2) the CE separation continues to function normally despite the presence of the extraction point opening.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method for extracting a droplet from fluid within a microfluidic column or channel, comprising the steps of:
    (a) providing a microfluidic device comprising:
        (i) a substrate comprising a channel comprising a liquid column and bounded by:
            (1) channel walls; or
            (2) surface property differences that constrain and direct the liquid column;
        (ii) an extraction point in the channel comprising an extraction opening and a refill opening opposite the extraction opening; and
        (iii) electrowetting electrodes on the substrate arranged for extracting a droplet from the liquid column at the extraction point;
    (b) separating particles or solute molecules of the liquid column into bands or zones; and
    (c) extracting, by use of the electrowetting electrodes, a first droplet comprising a band or zone of particles or solute molecules from the liquid column via the extraction opening while supplying a refill droplet into the liquid column via the refill opening.

2. The method of claim 1 further comprising:
    (d) transporting, by use of electrowetting electrodes, the first droplet to a separate evaluation site.

3. The method of claim 1 further comprising:
    (d) subjecting the first droplet to additional forces to cause additional separations of particles or solutes within the first droplet.

4. The method of claim 1, further comprising:
    (d) subjecting the first droplet to an electric field to cause the particles or solute molecules to migrate to one side of the droplet; and
    (e) splitting the droplet into separate droplets, with one separated droplet comprising the particles or solute molecules for conducting further analysis thereof.

5. The method of claim 1 wherein the channel is bounded by physical walls.

6. The method of claim 1 wherein the channel is bounded by surface property differences to constrain and direct the liquid column.

7. The method of claim 1 wherein step (c) is effected without the use of valves or pumps.

8. The method of claim 1 wherein step (c) is effected without the use of pneumatic effects.

* * * * *